US005417706A

United States Patent [19]

Chun

[11] Patent Number: 5,417,706

[45] Date of Patent: May 23, 1995

[54] ACUPUNCTURE TREATMENT OF COMMON BALDNESS

[76] Inventor: Pil H. Chun, 01501 Main St., Tewksbury, Mass. 01876

[21] Appl. No.: 109,422

[22] Filed: Aug. 20, 1993

[51] Int. Cl.[6] .............................................. A61B 17/34
[52] U.S. Cl. ..................................... 606/189; 606/204
[58] Field of Search ................. 606/189, 204; 128/907

[56] References Cited

U.S. PATENT DOCUMENTS 4,596,812 6/1986 Chidsey et al. ..................... 514/256

*Primary Examiner*—Michael H. Thaler
*Attorney, Agent, or Firm*—Robert I. Pearlman

[57] ABSTRACT

A specific acupuncture technique for the remedial treatment of various types of baldness by inserting acupuncture needles into selected acupuncture points on multiple meridians. The need for drugs, chemical treatment, surgery, herbs, etc. is eliminated.

8 Claims, 2 Drawing Sheets

ACUPUNCTURE TREATMENT OF COMMON BALDNESS

BACKGROUND OF THE INVENTION

The desire of both men and women to overcome alopecia, commonly referred to as baldness, is all too well known. Hair loss is most often considered to be of hormonal, emotional or uncertain etiology and is experienced by a large percentage of the population.

It has been suggested to employ drugs or chemical treatment. By way of example, U.S. Pat. No. 5,096,697 assigned to Lion Corporation of Japan teaches a cell-stimulating composition containing specified aliphatic alcohols having an odd number of carbon atoms as the effective ingredient. The Upjohn Company has in recent years marketed a drug sold under the Rogaine trademark to aid in hair growth. Such chemically related treatments have however had only modest success.

Additionally, the concept of transplanting patches of hair has been suggested as a baldness treatment. Such a technique requires surgical steps and likely pain.

A Russian article by S. N. Abramov, A. P. Zenkevich and N. N. Shinaev entitled "Microcirculation in the Skin in Patients with Different Forms of ALOPECIA in the COURSE OF REFLEX THERAPY" appeared in Vestn Dermatol Venerol, January, 1984. It reported that a decreased rate of capillary circulation existed with patients exhibiting alopecia as compared to a control group. Their patients were given reflex therapy. Acupuncture in conjunction with 133X2 Isotope was suggested to normalize disturbances in capillary circulation.

In a somewhat similar vein, another Russian author E. A. Ludyonsky ("Treatment of Alopecia", Vestn Dermatol Venerol, June 1983) proposes to treat alopecia by acupuncture by the May-Chua method in combination with corticotropin injections. The acupuncture is applied into sites of the posterior meridian as well a into auricular and scalp sites.

In the text "Acupuncture in Medical Practice" by Louise Oft Wensel, M. D., published 1980 by Reston Publishing Company, Inc., the authors speak of the use of acupuncture to treat alopecia areata which is caused by emotional reactions and characterized by patches of baldness asymmetrically located on the head. However, only a 30% success rate was reported for this specific treatment—a treatment which does not relate to common baldness.

Thus, while the prior art provides some suggestions as to the use of acupuncture for treating baldness, the prior art methods have had at best only limited usage and limited success.

BRIEF DESCRIPTION OF THE INVENTION

The present invention employs a specific and unique acupuncture techniques for the remedial treatment of baldness, such as male-pattern baldness, female pattern alopecia, drug induced alopecia and the types of baldness caused by collagin vascular diseases. This is done without the need for drugs, surgery, herbs, chemicals and like. The treatment is achieved normally by inserting an acupuncture needle into selected acupuncture points of multiple meridians which apparently effect the aforementioned types of baldness.

Optionally, the remedial techniques of acupressure, and/or inserting an acupuncture needle with a passing current (electro-acupuncture) can also be used at the selected acupuncture points in accordance with this invention. As used in the present specification, the term "acupuncture" denotes the use of needles, per se (classical acupuncture) as well as the more modern improvements of acupuncture with a pulse current passing through the needle or acupressure where stimulation to the key acupuncture points is supplied through the finger pressure of the clinician. In all three cases acupuncture stimulation is thus applied to the key acupuncture points identified as follows and the term "acupuncture stimulation" covers all these methods.

The acupuncture point locations used in the present invention fall as on the following meridians:

| | | |
|---|---|---|
| Stomach | Heart | Kidney |
| Spleen | Liver | Conception Vessel |
| Lung | Large Intestine | |

The nature and location of the meridians used in Chinese acupuncture are described in many texts, such as the following. The book "Acupuncture in Medical Practice", Louise O. Wensel, M. D., published 1980 by Reston Publishing (A Prentice Hall Company) is particularly noted, as well as the book by Felix Mann, M. B. entitled "Acupuncture, The Ancient Chinese Art of Healing and How it Works Scientifically", published 1973 by Vintage Books, a division of Random House, New York. Both books are herein incorporated by reference in the specification.

As is customary in acupuncture, the precise location on the meridians to insert the acupuncture needle or to apply acupressure is defined by units of measure called a cun or fen. A cun is approximately one inch in the average adult male and a fen is one-tenth of a cun. As described on page 16 of the Wensel text, a cun is proportionate to body size. A cun is the width of the widest part of a thumb. Accordingly, the length between two anatomical landmarks, such as the distance from the wrist to the elbow, is the same number of cun regardless of the seize of the body, e.g., it will be twelve cun for both an adult and a child even though it would vary significantly in centimeters.

The precise location of the acupuncture points is described in Table 1 in terms of the above measurement units well known to those skilled in the art of acupuncture.

DETAILED DESCRIPTION OF THE INVENTION

The exact mechanism by which the present acupuncture treatment technique works to treat baldness is not fully understood. The meridians of the kidney, lung, liver and supplemental points are related to stress. Acupuncture points of the lung meridian are relevant in invigorating and strengthening circulation and oxygenation of the skin. Liver meridian affects detoxification and regulation of the endocrine system. Kidney meridian affects the regulation of the genitourinary system and endocrine system.

DRAWINGS

Figures 1A, 1B:
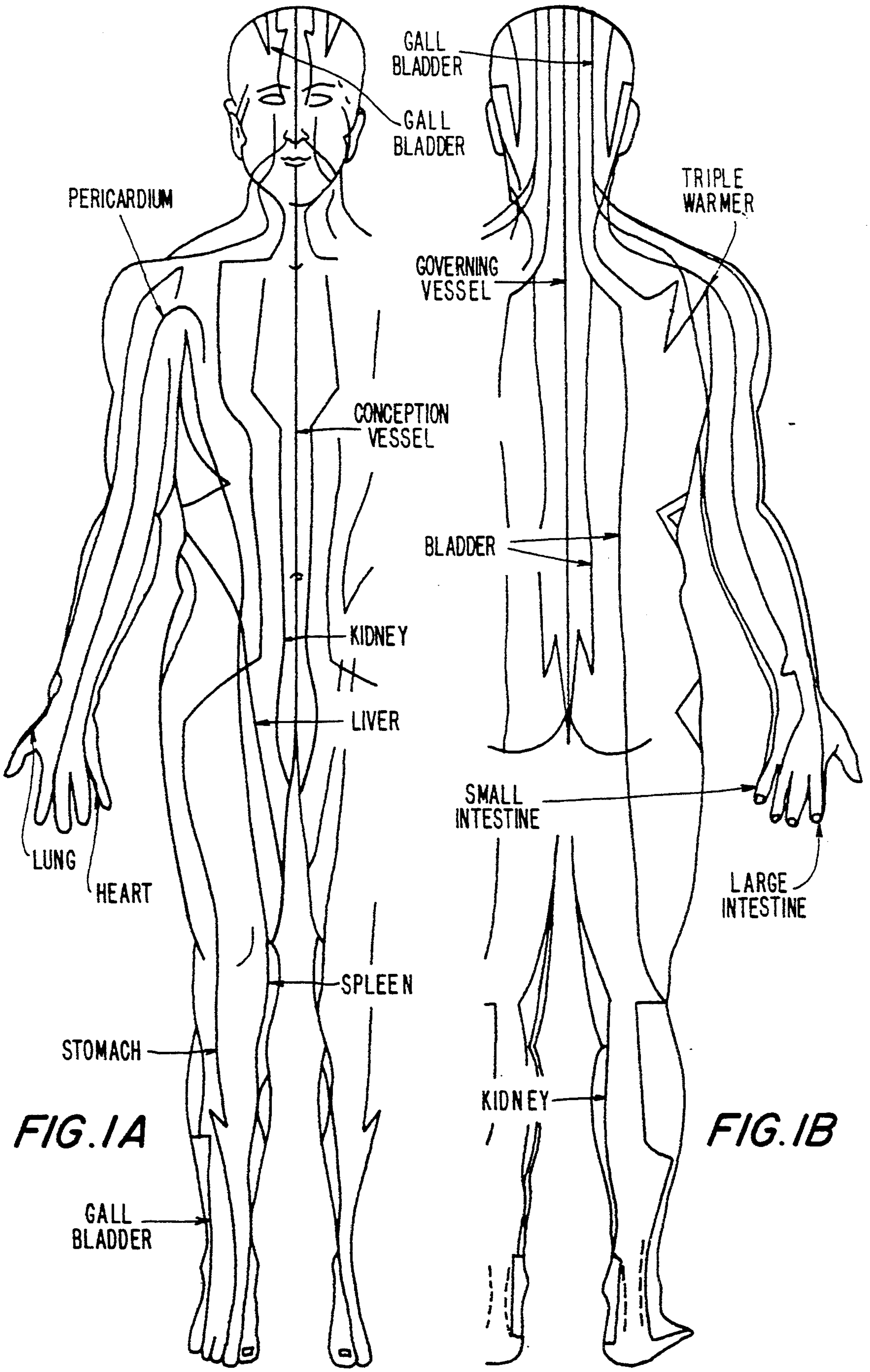

FIGS. 1*a* 1*b* represent a partial front and partial rear view of the art known meridians used in the practice of acupuncture and is taken from FIG. 19 of the Felix Mann book on "Acupuncture, The Ancient Chinese Art of Healing" identified previously.

Figures 2A, 2B:
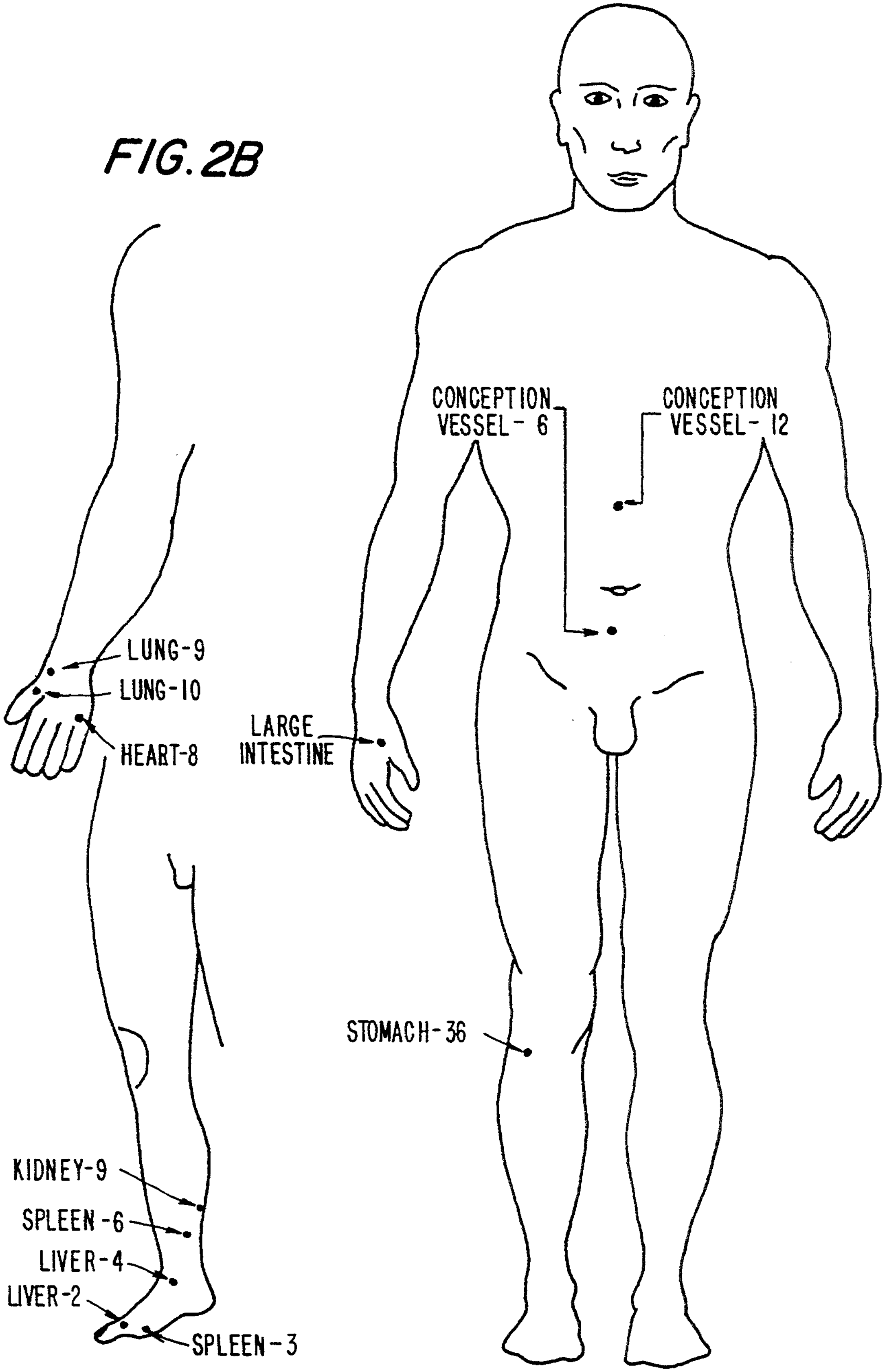

FIG. 2*a* and 2*b* show the twelve key acupuncture points and their location used in the practice of the present invention.

In the practice of the present invention, the location of the key acupuncture points on the specific patient to be treated must first be identified. This must be done by a person skilled in acupuncture utilizing the point locations in Table 1 as his guide.

When using acupuncture needles, a diameter of 0.1 to 0.5, preferably 0.2 to 0.4 millimeters will be suitable although this is up to the practitioners preference. A conventional needle length is employed, such as 4 to 6 centimeters, with its upper end normally somewhat wider to aide in finger grasping and/or the connection of electrical clips when applying current.

As an alternative to simple acupuncture, acupuncture needles in combination with a pulsed electrical current may be used. Such techniques (electro-acupuncture) are well known and are described in some detail in U.S. Pat. No 5,054,486 which publication is incorporated by reference herein. Nerve fibers can be excited by mechanical stimulation or electrical stimulation.

TABLE 1

Acupuncture Point and the Location of the Points

| Acupuncture Point | Location |
|---|---|
| Stomach-36 | 3 cun below the tuberosity of the tibia on the lateral aspect of the tibialis anterior muscle. |
| Spleen-3 | one-half cun behind the proximal end of the proximal phalange on the medial aspect of the foot at the anterior inferior border of the distal end of the first metatarsal bone. |
| Lung-9 | on the inferior margin of the lateral aspect of the greater multiangular carpal bone at the pulse point, being careful not to pierce the radial artery. |
| Lung-10 | over the middle of the first metacarpal bone on palmar surface. |
| Heart-8 | on the first skin crease on the palm between the fourth and fifth metacarpal bones. |
| Liver-2 | about 5 fen behind the web of the first to and the second toe, in front of the first and second joints of the digitorum pedis. |
| Liver-4 | 1 cun anteriorly from the medial malleolus between the tendons of the extensor hallucis longus muscle and the tibialis anterior muscle. |
| Large Intestine-4 | on the dorsum of the hand between the first and second metacarpal bones over the protuberance of the muscle on the radial side in the middle of the second metacarpal bone. |
| Kidney-9 | 5 cun above the posterior aspect of the medial malleolus. |
| Spleen-6 | 3 cun above the apex of the medial malleolus, behind the tibia (not to be used in pregnant patients). |
| Conception Vessel-6 | located 1.5 cun below the umbilicus. |
| Conception Vessel-12 | located 4 cun above the umbilicus or between the umbilicus and the costophrenic angle. |

After identification of the acupuncture points on the body of the patient, the patient should be put in a comfortable supine position and in a relaxed stated. The acupuncture needles (when using needle therapy) are inserted into the body in a random order. While not critical, best results are obtained with a 45 degree angle insertion other than liver-4 and large intestine-4 where a 90 degree angle insertion is preferred.

The depth of needle insertion depends on the anatomical location of the acupuncture point and the vitality of the patient as is customary in the practice of classical acupuncture. Experienced acupuncturists can sense the achievement of Te-Chi sensations (the classical sense of energization known in acupuncture) when the acupuncture needle is appropriately inserted. When a needle is inserted exactly into an acupuncutre point, the patient feels a sensation of heaviness, fullness and tingling as well as if a mild electrical current is passing along the meridian on which the point is located (see page 92 of the Wensell book identified previously). Very few acupuncture points require needle insertions deeper than 1.5 cun with penetrations of less than 0.5 cun most common.

After the insertion step is finished, the needles can be rotated in a clockwise or counterclockwise fashion. The order of insertion and rotation can be randomly chosen.

The preferred conditions of angle of insertion and direction of twisting of the needles is set forth regarding the use of double tonification and double sedation techniques described hereafter relative to Table 2. Tonification and sedation techniques, per se, have been known and described in the sa-am acupuncture technique. This technique is used to activate the underactive organs and to deactivate the overactive organs. It serves to enhance the effectiveness of the present invention. The direction for twisting the needle shown in Table 2 is for a male patient. The needle is twisted in the reverse direction for a female patient.

TABLE 2

Acupuncture Point and Double Tonification and Double Sedation Technique

| Acupuncture Point | Location |
|---|---|
| Stomach-36 | same direction of meridian pathway with 45 degree angle insertion<br>twist the needle to counterclockwise direction |
| Spleen-3 | same direction of meridian pathway with 45 degree angle insertion<br>twist the needle to counterclockwise direction |
| Lung-9 | same direction of meridian pathway with 45 degree angle insertion<br>twist the needle to counterclockwise direction |
| Lung-10 | opposite direction of meridian pathway with 45 degree angle insertion<br>twist the needle to clockwise direction |
| Heart-8 | opposite direction of meridian pathway with 45 degree angle insertion<br>twist the needle to clockwise direction |
| Liver-2 | same direction of meridian pathway with 45 degree angle insertion<br>twist the needle to counterclockwise direction |
| Liver-4 | 90 degree angle insertion |
| Large Intestine-4 | 90 degree angle insertion<br>twist the needle to counterclockwise direction |
| Kidney-9 | same direction of meridian pathway with 45 degree angle insertion<br>twist the needle to counterclockwise direction |
| Spleen-6 | same direction of meridian pathway with 45 degree angle insertion<br>twist the needle to counterclockwise direction |
| Conception Vessel-6 | same direction of meridian pathway with 45 degree angle insertion<br>twist the needle to counterclockwise direction |
| Conception Vessel-12 | 90 degree angle insertion<br>twist the needle to counterclockwise direction |

EXAMPLES

The acupuncture treatment of the present invention was tested on some 154 cases—127 male patients and 27 female patients. The particular observed problem areas for each patient are summarized by groupings as follows. Patients ranged in age from 20 to 78.

TABLE 3

| Grouping | Number of Males | Number of Females |
|---|---|---|
| Androgenetic | 116 | 0 |
| Stress | 2 | 0 |
| Combination of Androgenetic and Stress | 5 | 0 |
| Other - Alopecia Areata | 2 | 2 |
| Female Pattern Alopecia | 0 | 15 |
| Autoimmune Disease | 0 | 5 |
| Drug Induced | 2 | 5 |
| Total Patients Treated | 127 | 27 |

In each case the acupuncture procedure described previously were employed. Acupuncture needles alone were employed and inserted at the twelve key acupuncture points described in Table 1. The needles were rotated as described. Each individual treatment lasted approximately 15 to 30 minutes. Treatments were repeated approximately twice per week initially. After an initial period of about two months, treatment frequency can be reduced to about once per week depending on the patient's prognosis.

The tests showed positive results in 95% of the patients treated regardless of age and race. A cessation of hair loss was observed on average two to four weeks from the initiation of treatment. New hair growth was noted after an average of four to six weeks. This initial hair loss is thin, short and with less pigment.

The pattern of loss is from the frontal region to vertex and then to the occipital area. After the present treatment, the pattern of regrowth is in total reverse sequence, beginning at the occipital and advancing to the vertex and frontal regions. The new hair is thicker, longer and has a richer pigment.

Successful maintenance of both old and new hair varies by patient due to each patient's historical health background. Most of the patients start to show progress after three to four weeks of treatment. After reaching a steady state condition, treatment once per month is typically satisfactory.

What is claimed is:

1. A process for the treatment of baldness by the use of acupuncture which comprises applying acupuncture stimulation to the following acupuncture body points as identified by the denoted meridians

| | | |
|---|---|---|
| Stomach-36 | Liver-2 | Conception Vessel-6 |
| Kidney-9 | Liver-4 | Conception Vessel-12 |
| Lung-9 | Spleen-3 | Heart-8 |
| Lung-10 | Spleen-6 | Large Intestine-4. |

2. The process of claim 1 wherein acupuncture needles are inserted at the identified body points and are rotated.

3. The process of claim 2 wherein said needles range from 0.1 to 0.5 millimeters in diameter.

4. The process of claim 2 wherein a multiple of said needles is inserted at a 45 degree angle insertion.

5. The process of claim 2 wherein several needles are inserted in the same direction of their corresponding meridian pathway and several needles are inserted in an opposite direction in their corresponding meridian pathway.

6. The process of claim 2 wherein both double tonification and double sedation techniques are employed regarding the angle of acupuncture insertion and its direction of rotation.

7. The process of claim 1 wherein said acupuncture stimulation is effected by the use of acupressure.

8. The process of claim 1 wherein said acupuncture stimulation is effected by the use of acupuncture needles having a pulsed electrical current inserted at the acupuncture body points.

* * * * *